United States Patent [19]

Muraki et al.

[11] Patent Number: 4,813,428
[45] Date of Patent: Mar. 21, 1989

[54] DEVICE FOR DETECTING BREATHING

[75] Inventors: Yoshiya Muraki, Hasuda; Akinori Takahashi, Asaka, both of Japan

[73] Assignee: Fukuda Denshi Co., Ltd., Tokyo, Japan

[21] Appl. No.: 920,525

[22] Filed: Oct. 17, 1986

[51] Int. Cl.$^4$ ............................................... A61B 5/08
[52] U.S. Cl. ...................................... 128/721; 128/722; 128/782
[58] Field of Search ............... 128/721, 722, 725, 748, 128/774, 775, 781, 782, 715, 773; 340/573; 73/724, 718; 381/113, 56, 191, 174

[56] References Cited

U.S. PATENT DOCUMENTS

| | | | |
|---|---|---|---|
| 3,566,387 | 2/1971 | Schoener et al. | 128/204.23 |
| 3,727,606 | 4/1973 | Sielaff | 128/722 |
| 3,996,922 | 12/1976 | Basham | 307/400 |
| 4,516,428 | 5/1985 | Kowomi | 381/113 |

Primary Examiner—Edward M. Coven
Assistant Examiner—J. P. Lacyk
Attorney, Agent, or Firm—Toren, McGeady & Associates

[57] ABSTRACT

A breathing detection air bag is disclosed, which includes an air bag and a detector. The air bag includes a sponge body capable of being expanded and contracted with contraction and expansion of a pectoral or abdominal part of a person, a sponge cover enclosing the sponge body for preventing air contained in the pores of the sponge body from escaping from the pores, and a flange provided integrally with the edge of the sponge cover and an air guide tube for guiding an air stream caused by the expansion and contraction of the sponge body. The detector includes as oscillating film for causing a change in the electrostatic capacitance between it and a back electrode in response to a movement of air caused by expansion and contraction of the air bag, an electret capacitor microphone having a field-effect transistor for converting a change in the electrostatic capacitance into a change in voltage, and a pressure reduction film provided in front of the oscillating film for preventing mechanical saturation of the oscillating film when the extent of movement of air exceeds the distortion of the oscillating film.

1 Claim, 5 Drawing Sheets

4,813,428

DEVICE FOR DETECTING BREATHING

FIELD OF THE INVENTION

This invention relates to a device for detecting the status of breathing of a person and, more particularly, to a breathing detection device, which can detect the status of breathing through conversion of the extent of movement of air into an electric signal with an air bag.

PRIOR ART

Heretofore, electrocardiographs have been effectively utilized to determine the health condition of patients. It is necessary to have knowledge of the condition of the breathing organ, i.e., lungs, of a patient who has a breathing disorder. The condition of the breathing organ can be determined by grasping the status of breathing. e.g., the number of breathings per unit time, waveform of breathing, etc.

The pectoral or abdominal part of a person is moved as he or she breathes. This means that the pectoral or abdominal part represents the status of breathing. Therefore, if the movement of the pectoral or abdominal part can be grasped by some or other means, the condition of the breathing organ, i.e., the lungs, can be determined by detecting and recording the status of breathing.

This is very effective as a blood-free method of monitoring the breathing at the time of an actual surgical operation so long as there is no need of having information of the inside of the lungs.

From this viewpoint, the monitoring of the status of breathing of a patient has heretofore been performed by using an impedance system or a nasal foramen thermistor system. In the former system, the status of breathing is determined through measurement of the impedance of the surface of the patient's body. The impedance noted above is subject to changes with the breathing motion. The status of breathing is thus determined from the impedance changes.

In the latter system, a small thermometer is fitted in the nasal foramen. The status of breathing is determined through measurement of ambient temperature changes which are brought about as the patient breathes through the nose.

The status of breathing of a patient can be detected by the above methods. However, with the impedance system, it is difficult to detect the status of breathing accurately in case where the sensitivity to the breathing is low or when the breathing is not deep. Further, the nasal foramen thermistor system often makes use of an electrocardiogram electrode. In this case, the position of installation of the electrode is limited.

Further, although satisfactory breathing detection sensitivity can be obtained with the nasal foramen thermistor system, it is necessary in this case to fit a thermistor (i.e., thermometer) in the nose. Doing so spoils the appearance of the patient. In addition, pain is felt when the thermistor is held fitted for long time.

SUMMARY OF THE INVENTION

This invention has been intended in the light of the above problems, and its object is to provide a breathing detection device, which can readily detect breathing with high sensitivity.

To attain the above object of the invention, there is provided a breathing detection air bag, which comprises an air bag including a sponge body capable of being expanded and contracted with contraction and expansion of a pectoral or abdominal part of a man, a sponge cover enclosing the sponge body for preventing air contained in the pores of the sponge body from escaping from the pores and a flange provided integrally with the edge of the sponge cover and an air guide tube for guiding an air stream caused by the expansion and contraction of the sponge body, and a detector including an oscillating film for causing a change in the electrostatic capacitance between it and a back electrode in response to a movement of air caused by expansion and contraction of the air bag, an electret capacitor microphone having a field-effect transistor for converting a change in the electrostatic capacitance into a change in voltage, and a pressure reduction film provided in front of the oscillating film for preventing mechanical saturation of the oscillating film when the extent of movement of air exceeds the distortion of the oscillating film, a movement of air being caused with expansion and contraction of the air bag caused with breathing, the detector detecting the status of breathing through electric conversion of the extent of movement of air into an electric signal.

DETAILED DESCRIPTION OF THE PREFERRED EMBODIMENT

Now, the constitution and functions of the invention will be described in conjunction with an embodiment thereof consisting of an air bag 1 and a detector 7 with reference to the drawings.

Further, the description will be made with respect to the air bag 1, which is closely applied to the pectoral or abdominal part of a patient, and in which air is moved with its expansion and contraction in response to the contraction and expansion of the pectoral or abdominal part.

Figure 1:
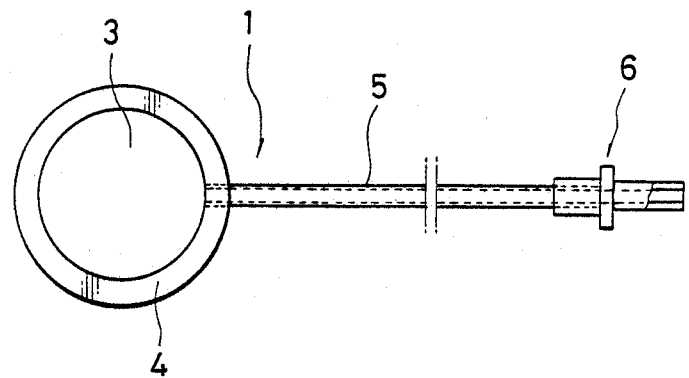
FIG. 1 is a plan view showing an air bag in an embodiment of the invention.
Figure 2:
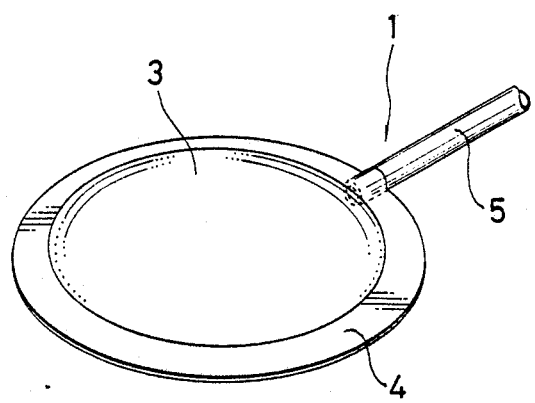
FIG. 2 is a perspective view showing an essential part of the air bag shown in FIG. 1.
Figure 3:
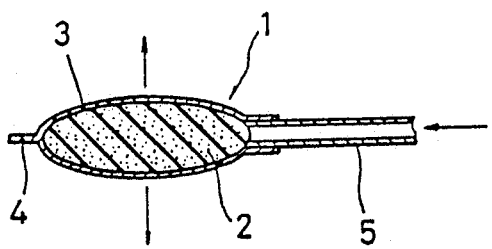
FIGS. 3 and 4 are sectional views showing the air bag shown in FIG. 2.
Figure 4:
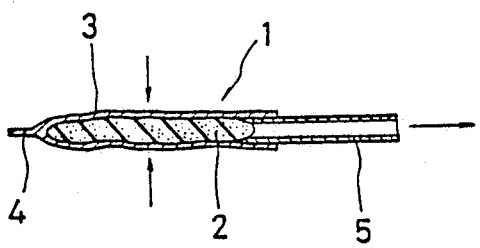

FIG. 1 is a plan view showing an embodiment of the breathing detection air bag according to the invention, FIG. 2 is a perspective view showing an essential part of the air bag shown in FIG. 1, and FIGS. 3 and 4 are sectional views of the air bag. Referring to the Figures, there is shown an air bag generally designated at 1. The air bag 1 comprises a sponge body 2, a sponge cover 3 of vinyl chloride, a flange 4 and an air guide tube 5.

The construction of the air bag will now be described in further detail. The sponge body 2 of the air bag 1 consists of polyurethane synthetic resin foam, which is soft and flexible and has numerous continuous pores. The vinyl chloride sponge cover 3 entirely encloses the sponge body 2 to prevent escapement of air contained in the continuous pores. The sponge body 2 enclosed in the sponge cover 3 is closely applied to the pectoral or abdominal part of the patient. In this state, it is expanded and contracted in correspondence to the movement of the pectoral or abdominal part of the patient caused by breathing. With the expansion or contraction of the sponge body 2, air is withdrawn into or forced out of the pores of the sponge body 2 enclosed in the sponge cover 3 through the air guide tube 5, as shown in FIGS. 3 and 4.

The flange 4 projects outwardly from the edge of the sponge cover 3 enclosing the sponge body 2. The air guide tube 5 extends from one end of the sponge body 2, and a connector 6 is mounted on the other end of the air guide tube 5. The flange 4 is provided so that the air bag 1 can be conveniently separated from the pectoral or abdominal part by pinching it after the air bag has been closely applied to the pectoral or abdominal part using adhesive tape.

Figure 5:
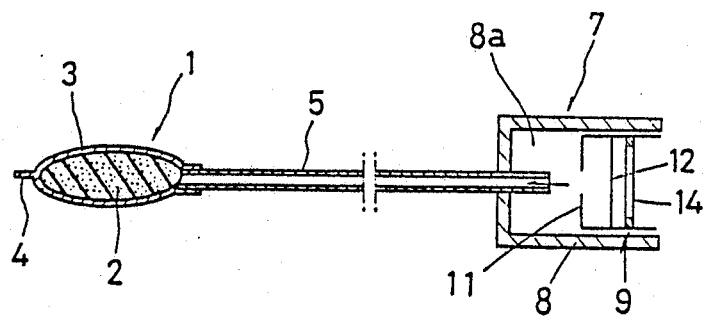
FIGS. 5 and 6 are sectional views showing an essential part of a breathing detection device comprising an air bag and a detector.
Figure 6:
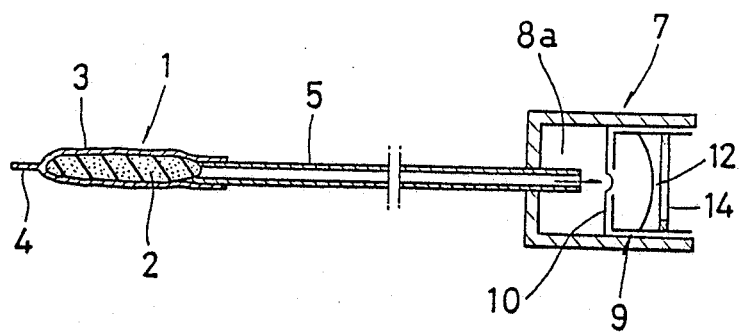

The connector 6 provided at the other end of the air guide tube 5 permits connection of the air guide tube 5 to a detector 7, as shown in FIGS. 5 and 6, which detects a movement of air due to expansion or contraction of the sponge body 2 and converts this movement of air into an electric signal. The movement (i.e., distortion) of the oscillating film 12 causes a change in the electrostatic capacitance between the oscillating film 12 and back electrode 14. The field-effect transistor 15 converts this change in the electrostatic capacitance into a change in voltage, which is displayed as the number of breathings per unit time of the waveform of breathing on a display (not shown), thus permitting the detection of the status of breathing.

This breathing detection device is used not only for the detection of the breathing, but it may also be effectively utilized for the detection of the cervical arterial wave in close contact with the top of the cervical arterial skin and for the detection of the finger tip sphygmic wave, apex cordis pulsations, etc.

As has been described in the foregoing, according to the invention, the status of breathing is detected by using an air bag. Therefore, there is no need of passing electricity to the skin surface of the living body, that is, electric insulation of the patient is ensured, which is desired from the standpoint of the safety Further, the air stream produced with the expansion and contraction of the air bag is detected with a detector. Therefore, satisfactory detection sensitivity can be obtained, and it is possible to ensure accurate detection of the breathing status.

Figure 7:
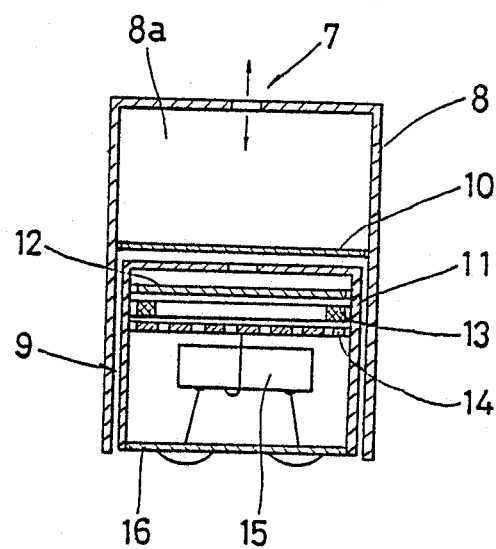
FIG. 7 is a sectional view showing a detector.
Figure 8:
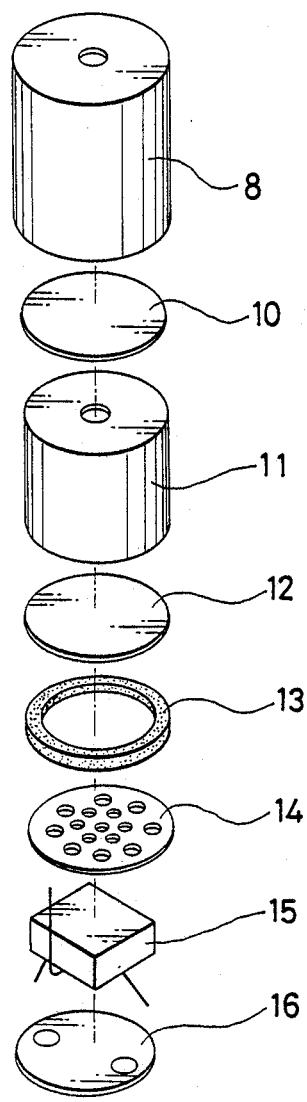
FIG. 8 is an exploded perspective view showing the detector.

Now, the construction of the detector 7 for converting a movement of air into an electric signal will be described with reference to FIGS. 7 and 8. Referring to the Figures, reference numeral 8 designates an outer cylinder of the connector 6. An electret capacitor microphone 9 is fitted in a lower portion of the connector outer cylinder 8. An air chamber 8a is defined between the outer cylinder 8 and the electrette capacitor microphone 9.

The electret capacitor microphone 9 comprises an electret capacitor microphone outer cylinder 11 which accommodates an oscillating film 12, a spacer 13, a back electrode 14 and a field-effect transistor 15 and has its lower open end closed by a base member 16. A pressure reduction film 10 is located over the electret capacitor microphone outer cylinder 11. The oscillating film 12, the spacer 13 and the back electrode 14 are attached, by any suitable means, to the side wall of the cylinder 11, so that the oscillating film 12 makes an airtight seal with the sidewall of the cylinder. The pressure reduction film 10, is an impermeable membrane and forms an airtight seal with the sidewall of the cylinder 8.

The oscillating film 12 is deformed in response to the extent of movement of air (causing a pressure change in the chamber 8a) which is introduced through the air guide tube 5 air chamber 8a with the expansion and contraction of the air bag 1. Thus, a change in the electrostatic capacitance between the oscillating film 12 and back electrode 14 is produced. This change in the electrostatic capacitance is converted by the field-effect transistor 15 into a change in voltage, which is displayed as the number of breathings per unit time or as the waveform of breathing by a display device (not shown). The maximum deformation extent of the oscillating film 12 of the electret capacitor microphone 9 is determined depending on its shape. Therefore, if the extent of movement of air (pressure change) causes the oscillating film 12 to exceed the maximum deformation level, the oscillating film 12 is mechanically saturated resulting in saturation of the output voltage.

To avoid this, it is made possible to readily adjust the sensitivity by installing the pressure reduction film 10 in front of the oscillating film 12 and by varying the thickness or material of the pressure reduction film 10. The resistance of the pressure reduction film 10 to flexing thereby absorbs a portion of the pressure changes caused by the contraction and expansion of the air bag 2. Hence, the pressure changes exerted on the oscillating film 12 are effectively reduced, thereby preventing saturation of the oscillating film 12.

Figure 9:
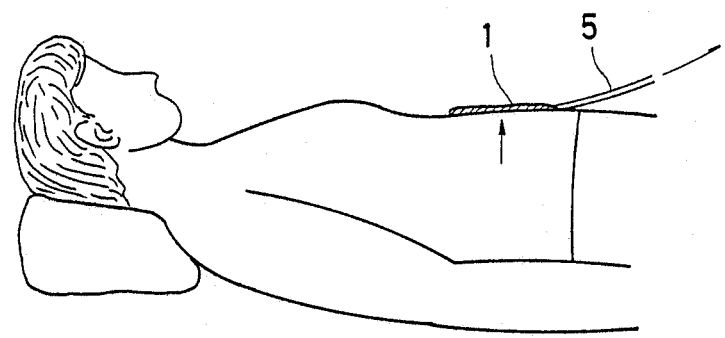
FIGS. 9 and 10 are views for explaining the air bag applied to a pectoral part of a patient in close contact therewith.
Figure 10:
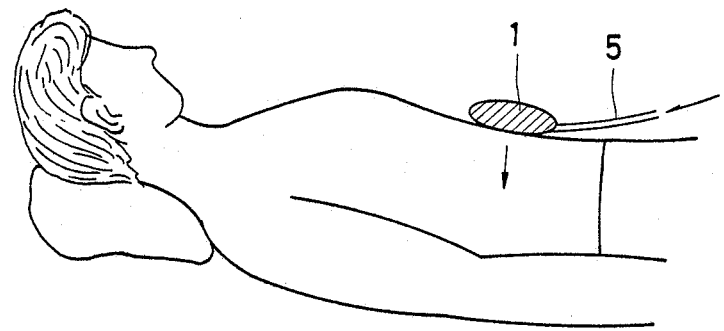

Now, a method of use of the breathing detection device comprising the air bag 1 and detector 7 will be described. As shown in FIGS. 9 and 10, the air bag is applied to the abdominal part of a patient with adhesive tape. With the expansive and contractive motions of the patient caused with the breathing thereof, the air bag is caused to undergo contraction and expansion. When the abdominal part is expanded, as shown in FIG. 9, the air bag 1 is urged and contracted so that air contained in the air bag 1 is forced out through the air guide tube 7 into the air chamber 8a, as shown in FIG. 6. The air forced into the air chamber 8a urged the oscillating film 12 via the pressure reduction film 10.

When the abdominal part is contracted, as shown in FIG. 10, the air bag 1 is expanded, and air that has been forced into the detector 7 is pulled back through the air guide tube 5 to the air bag 1, shown in FIG. 5, and the oscillating film 12 is restored to its initial position. The movement (i.e., distortion) of the oscillating film 12 produces a change in the electrostatic capacitance between the oscillating film 12 and back electrode 14. The transistor 15 converts the change in the electrostatic capacitance into a change in voltage. This change in voltage is displayed as the number of breathings per unit time and the waveform of breathing on a display (not shown). In this state, the status of breathing is detected.

The breathing detection may be used not only for the breathing detection as described above, but it may also be effectively utilized for the detection of the cervical arterial wave in close contact with the top of the cervical arterial skin and also for the detection of finger tip sphygmic wave, apex cordis pulsations, etc.

As has been described in the foregoing, according to the invention the status of breathing is detected using the air bag. Therefore, there is no need of applying electricity to the skin surface of a man, and safety can be ensured satisfactorily.

Further, since the air stream due to the expansion and contraction of the air bag is detected with the detector, the status of breathing can be detected accurately while ensuring satisfactory detection sensitivity.

What is claimed is:

1. A breathing detection apparatus comprising:
   (A) an airbag including:
      (a) a sponge body having pores therein for containing air, said sponge body being expandable and contractable in response to contractive and expansive motions of a body part of a person;
      (b) a sponge cover enclosing said sponge body for preventing air contained in the pores of said sponge body from escaping therefrom;
      (c) an air guide tube having one end connected to an opening in said sponge cover, said air guide tube guiding an air stream to and from said sponge cover caused by expansion and contraction of said sponge body; and
      (d) a flange provided integrally with a peripheral edge of said sponge body; and
   (B) a detector coupled to another end of said air guide tube for converting said air stream to a variable voltage, a level of said variable voltage being proportional to a flow rate and direction of said air stream, said detector including:
      (a) an open-ended housing, said air guide tube being connected to a closed end of said housing;
      (b) an electret capacitor microphone closing said open-end of said housing, said electret capacitor microphone comprising:
         (1) a housing having an aperture therein opening into said open-ended housing;
         (2) an oscillating film spaced from and opposite to said aperture, said film forming a seal with sides of said housing;
         (3) a back electrode spaced behind said oscillating film, said back electrode and said oscillating film having an electrostatic capacitance which varies with movement of said oscillating film;
         (4) a field-effect transistor connected to said back electrode for converting changes in said electrostatic capacitance to said variable voltage, and
      (c) a pressure reduction film mounted in said open-ended housing between said microphone and said closed end of said open-ended housing, said pressure reduction film being a continuous air impermeable membrane and forming an airtight seal with sides of said open-ended housing;
   whereby movement of said air stream causes pressure changes in said housing which, in turn, cause said oscillating film to deflect changing the electrostatic capacitance of the oscillating film and the back electrode, this change in capacitance being converted into the variable voltage by said field effect transistor, and whereby a resistance to flexing of said pressure reduction film reduces the pressure exerted on said oscillating film thereby preventing saturation of said oscillating film.

* * * * *